United States Patent [19]

Lalin

[11] 4,389,372
[45] Jun. 21, 1983

[54] PORTABLE HOLDER ASSEMBLY FOR GAS DETECTION TUBE

[76] Inventor: Hill S. Lalin, 10 Bonita Ter., Wayne, N.J. 07470

[21] Appl. No.: 282,436

[22] Filed: Jul. 13, 1981

[51] Int. Cl.$^3$ ............................ G01N 1/22; B01L 9/00
[52] U.S. Cl. ........................................ 422/88; 422/86; 422/104
[58] Field of Search ..................... 422/58, 59, 70, 84, 422/85, 86, 88, 104; 55/386; 210/198.2

[56] References Cited

U.S. PATENT DOCUMENTS

| | | | |
|---|---|---|---|
| 2,234,499 | 3/1941 | McAllister | 422/86 |
| 2,429,694 | 10/1947 | King | 422/86 |
| 2,631,088 | 3/1953 | Guild | 422/88 |
| 3,388,975 | 6/1968 | Wallace | 422/59 |
| 3,539,302 | 11/1970 | Dreckmann | 422/86 |
| 3,585,963 | 6/1971 | Hiszpanski | 422/86 |
| 4,040,783 | 8/1977 | Collin | 23/232 R |
| 4,159,304 | 6/1979 | Shono | 422/86 |

Primary Examiner—Michael S. Marcus

[57] ABSTRACT

A portable holder assembly in combination with one or more gas detection tubes each of which contain chemical sorbent material. Each sorbent tube has a tapered neck at each opposite end with an opening adapted for drawing ambient gas through the sorbent material. The holder assembly comprises an open ended hollow tubular shell surrounding each gas detection tube, end fitting means for closing the open ends of each shell to form a closed chamber between each shell and each gas detection tube and an O-ring mounted in each end fitting means in surrounding engagement with the tapered neck of each tube for suspending each tube within each shell and for sealing off the open ends of each tube from the closed chamber.

8 Claims, 5 Drawing Figures

PORTABLE HOLDER ASSEMBLY FOR GAS DETECTION TUBE

The present invention relates to a portable holder assembly for an arrangement of one or more gas detection tubes for use in an air sampling system.

Within the past ten years a new field of air sampling has developed utilizing gas detection tubes filled with various chemical sorbent materials for detecting small concentrations of gaseous impurities in air or other gases. The gas detection tubes are used in combination with a pump for drawing ambient air or other gaseous composition through each tube at a predetermined flow rate to provide an indication of the presence of a given impurity as well as to provide a measure of the concentration of the impurity over a given test sampling time period.

Most gas detection tubes are designed in the form of an elongated cylindrical enclosure of transparent material such as a pyrex glass into which the sorbent material is placed before the opposite ends are drawn and sealed. The diameter and length dimensions of the detection tubes will vary depending upon the nature of the gaseous impurity to be detected and the composition of the sorbent material. Accordingly, a wide variety of tubes of different diameter and length are commonplace. Many manufacturers of air sampling systems which utilize gas detection tubes offer tube holders to secure and protect the detection tubes during the test period and to facilitate the attachment of the detection tube upon an operator's clothing. The conventional tube holder is a tubular member of a plastic resinous composition containing a boss at one end and a rubber collar at the other end. The gas detection tube is inserted in the tube holder after the ends are broken with the rubber collar mounted over one of the open ends. The tube holder boss is coupled to a length of tubing extending from a pump. An alternative arrangement which is commercially used couples the gas detection tube through an O-ring or other sealant to the tube holder boss. The tube holder boss is likewise coupled to a length of tubing extending from the pump. One end of the tube holder has an air passageway through which ambient air may be suctioned.

The present day tube holder design renders it difficult if not impossible to flow calibrate the gas detection tube in place within the air sample system as a basis for measuring impurity concentration. Once the gas detection tube is assembled within the tube holder it is essential for accuracy of the impurity concentration measurement that the operator be assured that the test will be a measure of only impurities through the gas detection tube. Accordingly, it is desirable to be able to run a calibration test of the holder assembly both without the detection tube and with the detection tube in place. Prior tube holder designs do not readily permit a calibration test of the air sampling system. Also, in the typical tube holder design the broken off end of the gas detection tube is often in physical contact with the tube holder housing permitting broken glass particulates to be drawn into the pump.

In accordance with the tube holder assembly of the present invention calibration of the air sampling system is readily facilitated both with and without the gas detection tube. Moreover, the tube holder assembly readily accommodates a whole family of difficult size gas detection tubes in a variety of arrangements using one or more gas detection tubes in combination.

It is therefor, the principal object of the present invention to provide a portable holder assembly for a gas detection tube for use in an air sampling system which permits calibration of the system with the gas detection tube in line and with the gas detection tube removed.

It is another object of the present invention to provide a portable holder assembly for a gas detection tube for use in an air sampling system in which air or other gas drawn into the system can pass only through the gas detection tube.

It is yet a further object of the present invention to provide a portable holder assembly for a multiple number of gas detection tubes which may be arranged in a variety of combinations such as in series or parallel with respect to one another for performing multiple air sample tests simultaneously.

Other objects and advantages of the present invention will become apparent from the following detailed description of the invention when read in conjunction with the accompanying drawings of which:

Figure 1:
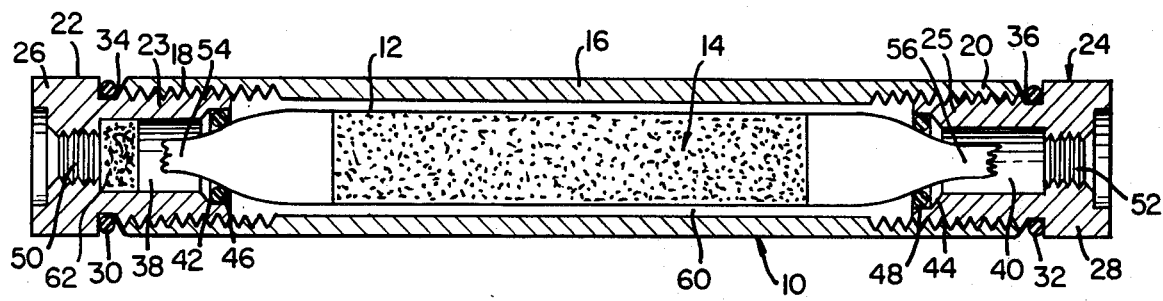
FIG. 1 is a longitudinal cross-section of the tube holder assembly for a single gas detection tube in accordance with the present invention.

Referring now to FIG. 1 which illustrates the design of the tube holder assembly 10 of the present invention for securing a gas detection tube 12 containing a sample of chemical sorbent material 14. The tube holder assembly 10 comprises a tubular shell 16 of a given length and diameter to accommodate the gas detection tube 12. The gas detection tube 12 may be of any size diameter provided it is smaller than the diameter of the tubular shell 16. A number of tubular shells 16 of varying lengths will permit all commercially available detection tubes to be accommodated. In addition, the use of a variety of end fittings to be hereinafter discussed permits the operator to establish any combination of multiple gas detection tube configurations. The tubular shell 16 is hollow and open at its opposite ends 18 and 20 respectively. Each open end has internal threads which extend a predetermined axial distance to permit the gas detection tube 12 to be securely suspended from the opposite ends 18 and 20 by the use of end fittings as hereafter explained as well as to allow for take-up of relatively substantial variations in gas detection tube length.

An end fitting 22 and 24 is inserted at each opposite end 18 and 20 of the tubular shell 16. Each end fitting 22 and 24 has an externally threaded male section 23 and 25 for engaging the internal threads in the shell 16 and an enlarged disk shaped end section 26 and 28 respectively. A pair of O-rings 30 and 32 are fitted in grooves 34 and 36 intermediate the male sections 23 and 25 and the corresponding end sections 26 and 28. The male sections 23 and 25 each have an internal axially disposed bore 38 and 40 of cylindrical configuration with a beveled end 42 and 44. The beveled ends 42 and 44 provide a seat for O-rings 46 and 48 respectively. The end sections 26 and 28 each have a threaded opening 50 and 52 communicating with and extending from the bore 38 and 40 of the male sections 23 and 25. The threaded openings 50 and 52 are adapted to receive further end fittings as will be hereafter explained.

The gas detection tube 12 with its necked ends 54 and 56 broken open by any conventional means (not shown) is loaded into the tubular shell 16 after one of the end fittings 22 or 24 is threaded in place. The inserted open necked end 54 or 56 of the gas detection tube 12 is seated within the O-ring 46 or 48 corresponding to whichever end fitting 22 or 24 is in place. The uninserted end fitting is then threaded into the opposite end of the shell 16 for automatically seating and suspending the gas detection tube 12 between the O-rings 46 and 48. With the O-rings 46 and 48 seated around the open necked ends 54 and 56 the gas detection tube 12 is effectively sealed at both ends from any contamination or from ambient gas leakage into the space 60 between the gas detection tube 12 and the tubular shell 16.

The threaded openings 50 and 52 in the end fittings 22 and 24 provide the only access to the chemical sorbent composition 14 in the gas detection tube 12. A filter 62 may be inserted into either bore 38 or 40 of the end fittings 22 or 24 located at the downstream end of the air sampling system to prevent any particulate matter from the broken neck of the gas detection tube from being drawn into the pump (not shown).

Figure 2:
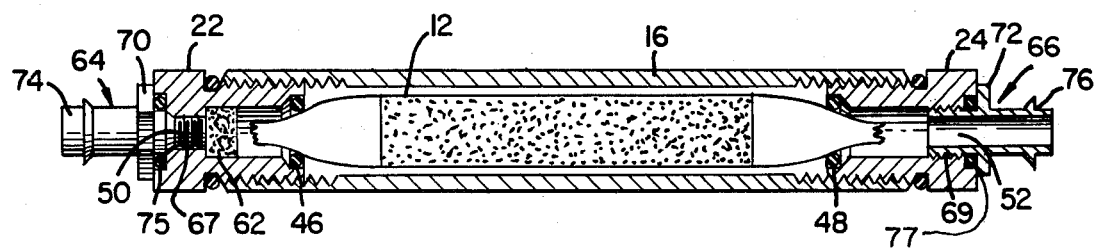
FIG. 2 is a longitudinal cross-section of the tube holder assembly similar to FIG. 1 with barb fittings for in-line use known in the art as a trap configuration.

A barb fitting 64 and 66 may be threadably inserted into each opening 50 and 52 respectively as shown in the in-line or trap configuration of FIG. 2. Common reference numerals are used to identify equivalent parts in each of the Figures. The barb fittings 64 and 66 each have a longitudinal bore extending therethrough and comprise a threaded shank section 67 and 69 for engaging the female threads in openings 50 and 52; an enlarged collar 70 and 72 surrounding each shank section and having the shape of a hex nut for locking the fittings 64 and 66 in place and a barbed head 74 and 76 adapted for being mounted inside flexible tubing (not shown) which extends from the suction pump forming a conventional air sampling system (not shown). An O-ring 75 and 77 is preferably fitted over each threaded shank section in abutment with each enlarged collar for sealing the two fittings at each end of the tubular shell 16 against leakage.

Figure 3:
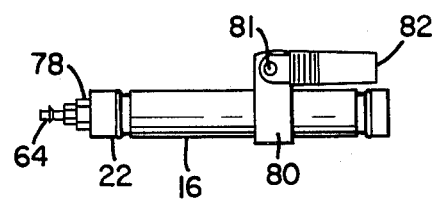
FIG. 3 is a side view illustration of the tube holder assembly of the present invention in a fixed orifice configuration.

An alternative arrangement is simply formed by removing one of the barb fittings 66 from the end fitting 24 and interposing a fixed orifice coupling 78 between the barb fitting 64 and the end fitting 22 as shown in FIG. 3. As a further alternative a variable orifice member (not shown) may be used in substitution for the fixed orifice coupler 78 for certain variable flow conditions. For attachment to the operator's clothing a strap 80 may be fitted over the tubular shell 16 and secured through an eyelet 81 to a manually operated hinge type clip 82.

Figure 4:
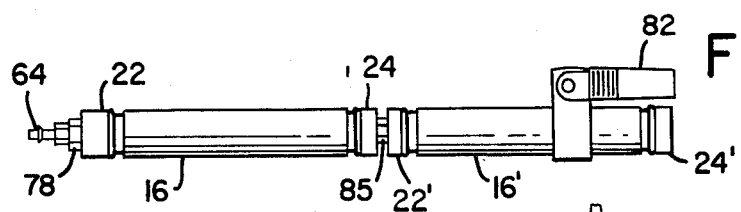
FIG. 4 is another side view illustration of the tube holder assembly of the present invention for use in combination with two gas detection tubes in a series arrangement.

A multiple tube configuration for the tube holder assembly of the present invention is shown in FIG. 4. Two identical tubular shells 16, 16' are connected in series by joining the end fitting 24 from the first tubular shell 16 to the end fitting 22' of the second tubular shell 16' by means of a hollow connector fitting 85 which has male threads on opposite sides for engaging the female threads in each end fitting 24 and 22'. It should be understood that in each tubular shell 16 and 16' a gas detection tube 12 would be suspended between the two O-ring seals as shown in FIGS. 1 and 2.

Figure 5:
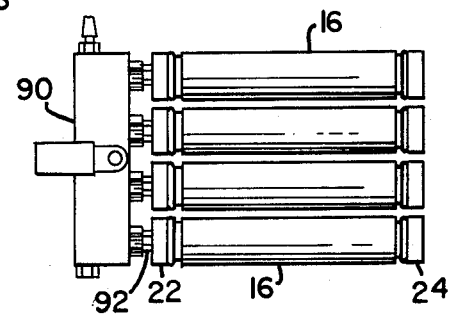
FIG. 5 is yet another side view illustration of the tube holder assembly of the present invention for use in combination with a multiple number of gas detection tubes in a parallel arrangement.

An even further multiple tube arrangement for the tube holder assembly of the present invention is shown in FIG. 5. Four identical tubular shells 16 are shown, each having identical end fittings 22 and 24 for sealing the opposite ends of the tubular shells 16 and for suspending a gas detection tube from such opposite ends. All four tubular shells are connected in parallel to a common manifold 90 through a fixed orifice manifold fitting 92.

The tube holder assembly 10 of the present invention readily permits calibration of a gas detection tube in place. An operator need only secure a gas detection tube 12 within a shell 16 between the two end fittings 22 and 24 with one of the end fittings 22 coupled to a barb fitting 64. The barb fitting 64 is connected to form an air sampling system by connection to a pump through a length of tubing. Ambient air is drawn through the gas detection tube 12 from the open end fitting 24 thereby allowing the tube 12 to be calibrated in place.

The air sample system may also be calibrated without the gas detection tube in place. This is done by removing the gas detection tube 12 from the shell 16 and reinserting the end fittings 22 and 24 which are screwed in until the O-rings 30 and 32 seall off the tubular shell and the end fittings 22 and 24 against the O-rings 30 and 32.

What is claimed is:

1. In combination, a portable gas detection tube holder assembly and at least a first and second gas detection tube supported by said holder assembly in a series or parallel arrangement relative to one another with each gas detection tube having an elongated body within which a chemical sorbent material is stored, a tapered neck portion at opposite ends of said elongated body and an opening in each neck portion adapted for drawing ambient gas through said sorbent material, said gas detection tube holder assembly comprising:
   a clear hollow tubular shell surrounding each gas detection tube in a spaced apart relationship with each shell having opposite open ends;
   end fitting means for closing the open ends of each shell to form a closed chamber between each shell and each gas detection tube with each end fitting means having a longitudinal bore for communicating with the opening in each neck portion of each gas detection tube; means for coupling in series or parallel arrangement said first and second gas detection tubes and said respective tubular shells to one another through an end fitting means for each gas detection tube such that said first gas detection tube has one open neck portion communicating with one open neck portion in said second gas detection tube; and an O-ring mounted in each end fitting means in surrounding engagement about the tapered neck portion of each gas detection tube at each opposite end thereof such that each gas detection tube is suspended between a pair of O-rings in longitudinal alignment with the longitudinal bore of the end fitting means and for sealing off the open ends of each gas detection tube from the surrounding closed chamber.

2. The combination as defined in claim 1 wherein each end fitting means comprises a male section for coupling to an open end of said tubular shell and an enlarged collar extending from said male section with said longitudinal bore extending through said male section and said collar.

3. The combination as defined in claim 2 wherein each male section has beveled end upon which said O-ring is mounted.

4. The combination as defined in claim 2 further comprising a hollow barb fitting having an externally threaded shank for threadably engaging said longitudinal bore in said collar at one end of said tubular shell and a barbed head adapted for connection to a length of tubing extending from a pump in forming an air sampling system.

5. The combination as defined in claim 2 further comprising a coupling having a fixed orifice interposed between an end fitting and a brab fitting.

6. The combination as defined in claim 2 further comprising an additional O-ring mounted on each end fitting means adjacent to each collar on the side thereof facing the tubular shell for sealing said tubular shell when calibrating said shell without the presence of a gas detection tube.

7. The combination as defined in claim 2 wherein said means for coupling comprises a hollow coupling having external threads at opposite ends for connecting the enlarged collar of one end fitting means in the first gas detection tube to the enlarged collar of another end fitting means in the second gas detection tube.

8. The combination as defined in claim 2 wherein said means for coupling comprises a common manifold and means for connecting the common manifold to one end fitting means for each gas detection tube.

* * * * *